United States Patent
Hekimian (10) Patent No.: US 6,651,676 B1
(45) Date of Patent: Nov. 25, 2003

(54) DENTAL FLOSS PACKAGE WITH VERIFICATION SYSTEM, AND METHOD OF VERIFYING FLOSSING REGIMEN

(75) Inventor: Christopher D. Hekimian, 28 O'neill Dr., Apt. 5, Gaithersburg, MD (US) 20877

(73) Assignees: Christopher D. Hekimian, Germantown, MD (US); Behnam Manesh, Potomac, MD (US)

( * ) Notice: Subject to any disclaimer, the term of this patent is extended or adjusted under 35 U.S.C. 154(b) by 17 days.

(21) Appl. No.: 10/042,318

(22) Filed: Jan. 11, 2002

(51) Int. Cl.[7] ................................................ A61C 15/00
(52) U.S. Cl. .................................................... 132/321
(58) Field of Search ............................... 132/321, 324, 132/200, 329; 434/263; 206/534, 538

(56) References Cited

U.S. PATENT DOCUMENTS

| | | | |
|---|---|---|---|
| 2,809,458 A | * 10/1957 | Wilbourn | 132/321 |
| 3,126,129 A | 3/1964 | Weinberg | |
| 3,897,796 A | 8/1975 | Erickson | |
| 4,034,770 A | 7/1977 | Trecker | |
| 4,878,845 A | 11/1989 | Lindsay et al. | |
| 5,159,943 A | * 11/1992 | Richards et al. | 132/321 |
| 5,174,451 A | * 12/1992 | Niven | 206/534 |
| 5,316,028 A | 5/1994 | Flemming | |
| 5,365,874 A | 11/1994 | Dorfman | |
| 5,629,527 A | 5/1997 | Levitt et al. | |
| 5,826,594 A | 10/1998 | Sokal | |
| 5,865,197 A | * 2/1999 | Bible et al. | 132/321 |
| 5,913,418 A | 6/1999 | Singh | |
| 6,016,816 A | 1/2000 | Ariagno | |
| 6,039,213 A | * 3/2000 | Sloan et al. | 222/39 |
| 6,412,632 B1 | * 7/2002 | Shrader | 206/459.1 |

* cited by examiner

Primary Examiner—John J. Wilson
Assistant Examiner—Robyn Kieu Doan
(74) Attorney, Agent, or Firm—Sughrue Mion, PLLC

(57) ABSTRACT

A dental floss package includes a dispenser for dispensing a dental floss. The dental floss has a plurality of floss segments. Each floss segment is of a length that is suitable for a single flossing. Adjacent floss segments are different colors. And one of the floss segments is specially marked so that it is distinguishable from the other floss segments. A location indicator is provided to indicate the specific location of the specially marked floss segment along the length of the dental floss from the leading end of the dental floss. The location of the specially marked floss segment is indicated as the number of floss segments into the length dental floss. The location indicator is removably attached to the dispenser so that it can be concealed from the user. When the user encounters the specially marked floss segment, the length of the flossing regimen is calculated and compared to the location information on the location indicator.

15 Claims, 7 Drawing Sheets

| END START | JAN | FEB | MAR | APR | MAY | JUN | JUL | AUG | SEP | OCT | NOV | DEC | JAN | FEB |
|---|---|---|---|---|---|---|---|---|---|---|---|---|---|---|
| JAN | 0 | 0 | L-1 Y-2 | | | | | | | | | | | |
| FEB | | 0 | L-2 Y-3 | L-1 Y-2 | | | | | | | | | | |
| MAR | | | 0 | 0 | 1 | | | | | | | | | |
| APR | | | | 0 | 1 | 1 | | | | | | | | |
| MAY | | | | | 0 | 0 | 1 | | | | | | | |
| JUN | | | | | | 0 | 1 | 1 | | | | | | |
| JUL | | | | | | | 0 | 0 | 0 | | | | | |
| AUG | | | | | | | | 0 | 0 | 1 | | | | |
| SEP | | | | | | | | | 0 | 1 | 1 | | | |
| OCT | | | | | | | | | | 0 | 0 | 1 | | |
| NOV | | | | | | | | | | | 0 | 1 | 1 | |
| DEC | | | | | | | | | | | | 0 | 0 | 0 |

DENTAL FLOSS PACKAGE WITH VERIFICATION SYSTEM, AND METHOD OF VERIFYING FLOSSING REGIMEN

BACKGROUND OF THE INVENTION

Apparatuses and methods consistent with the present invention relate in general to dental floss packaging, and more particularly to a dental floss package including a built in flossing regimen verification system.

It is a challenge shared by dental professionals and parents to instill good flossing habits in children and young people. This challenge is difficult since the rewards of flossing (as important as they are) seem very distant and remote, especially from the child's perspective. Furthermore, most children do not find flossing to be an enjoyable activity.

Conventional attempts to encourage regular flossing habits have focused on making the dental floss and the packaging more appealing to the user. For example, dental floss (which includes cylindrical flosses and dental tapes) may be flavored and/or colored. Dental floss may also be provided in varying diameters and different fiber structures. The packaging efforts primarily involve making the dispensers more convenient.

Although the conventional approaches noted above are generally believed to make flossing more appealing to the user, they are not without shortcomings. Namely, a need still remains to verify that a regular flossing regimen has in fact been followed. Such a verification system could be advantageously used as a basis for establishing a positive feedback reward system.

SUMMARY OF THE INVENTION

The invention resides in a multi-colored dental floss that has a plurality of floss segments. Adjacent floss segments are colored differently, and each floss segment defines a usable length of the dental floss for a single flossing.

The invention also resides a dental floss package. The package includes a dispenser that contains a dental floss. The dental floss has a plurality of floss segments, and one of the floss segments is specially marked. A location indicator is also provided. It indicates the location of the specially marked floss segment along the length of the dental floss.

The invention also resides in a method to verify adherence to a flossing regimen. The method involves providing a dental floss having a plurality of floss segments, and one of the floss segments being specially marked. A location indicator is provided that sets forth location information of the specially marked floss segment along the length of the dental floss. A flossing regimen is initiated on a start date. The flossing regimen continues until an end date on which the specially marked floss segment is encountered. The length of the flossing regimen is determined. And this determination is compared to the location information.

The above and other features of the invention including various and novel details of construction and process steps will now be more particularly described with reference to the accompanying drawings and pointed out in the claims. It will be understood that the particular dental floss package and method for verifying adherence to a flossing regimen embodying the invention is shown by way of illustration only and not as a limitation of the invention. The principles and features of this invention may be employed in varied and numerous embodiments without departing from the scope of the invention.

DETAILED DESCRIPTION OF AN ILLUSTRATIVE, NON-LIMITING EMBODIMENT OF THE INVENTION

I. The Colored Floss Segments

Figure 1:
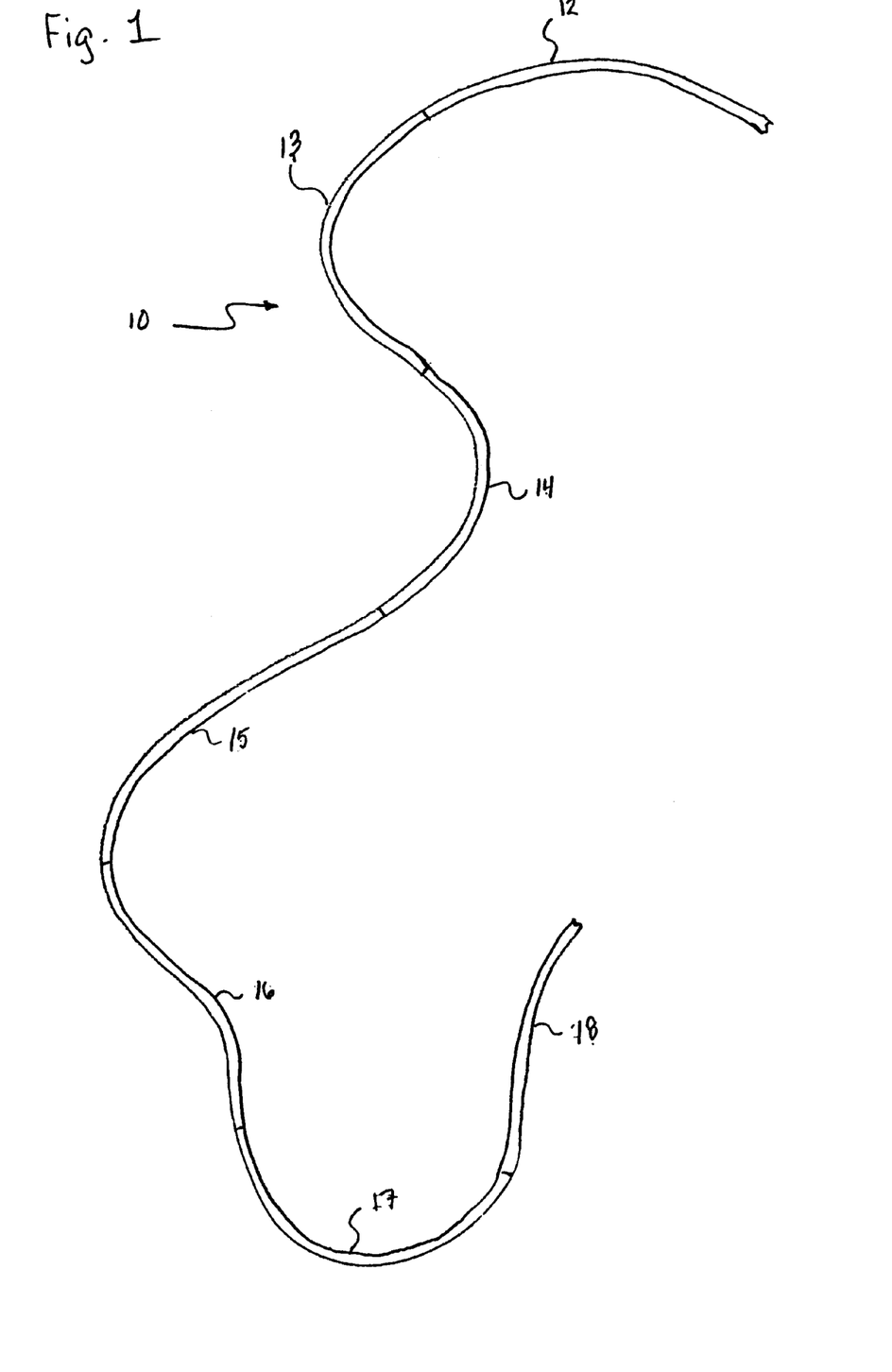
FIG. 1 is a perspective view of a dental floss according to an illustrative, non-limiting embodiment of the present invention.

FIG. 1 shows a portion of dental floss 10 according to an illustrative, non-limiting embodiment of the present invention. The dental floss 10 is a thread like member that includes a plurality of colored floss segments, e.g., 12–18. Each floss segment has a uniform length that is suitable for use during a single flossing. Preferably, but not necessarily, the uniform length is set to a recommended length for children's use by a dental professional.

Additionally, adjoining floss segments have different colors to provide a visual indication of the proper length of floss to be used. For example, floss segment 12 may be blue, and floss segment 13 may be red. The child would first dispense, sever, and floss with the blue floss segment 12. Then on the following day, assuming that the child is flossing on a daily basis, the child would dispense, sever, and floss with the red floss segment 13. In this way, the colored floss segments allow a child to easily remove a proper length of floss to perform each flossing. The colored floss segments also provide a basis for the floss regimen verification system, which is discussed in detail below.

The invention is not limited to a particular range of colors for the floss segments. And it is to be appreciated that the sequencing of colors may vary along the length of the dental floss 10. Furthermore, the dental floss 10 may be fabricated from convention materials, including stranded fibers, tapes, and ribbons, which may be waxed or unwaxed.

II. The Dispenser

Figure 2:
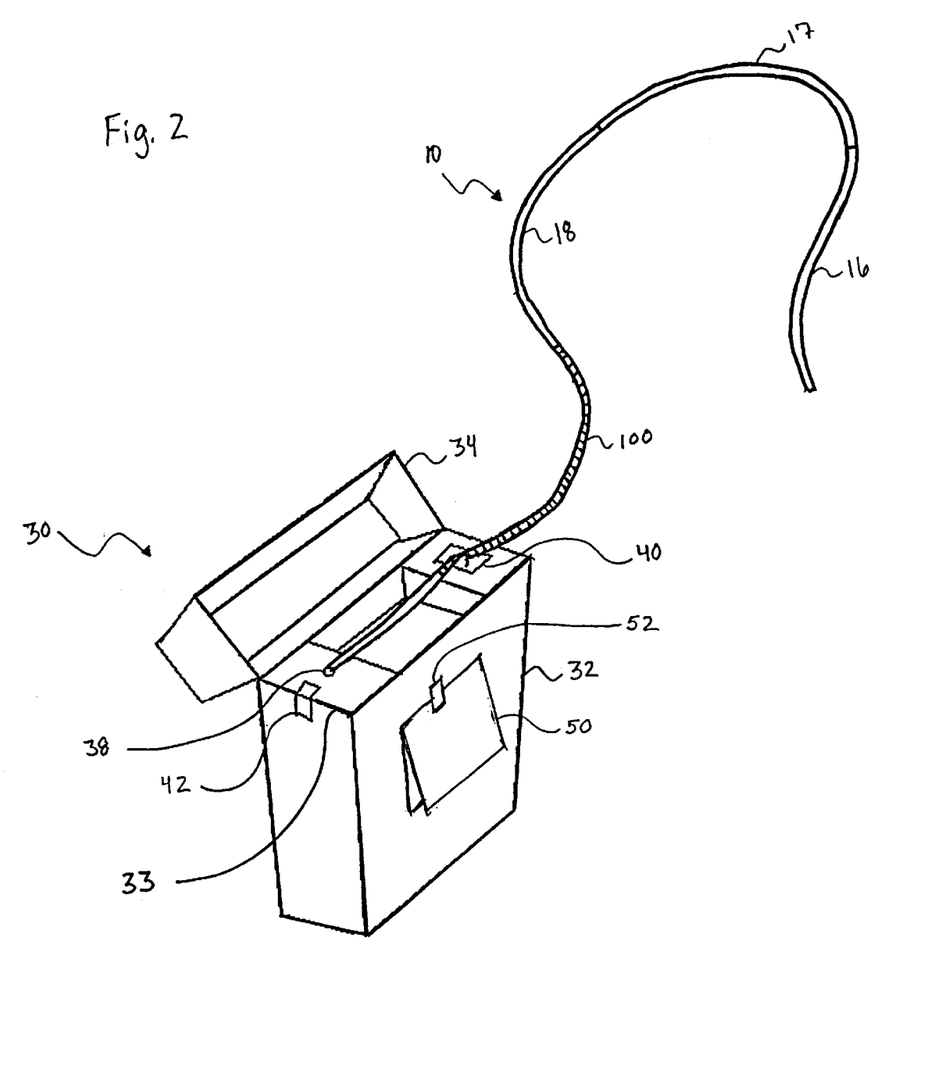
FIG. 2 is a perspective view of a dental floss package according to an illustrative, non-limiting embodiment of the present invention.
Figure 3:
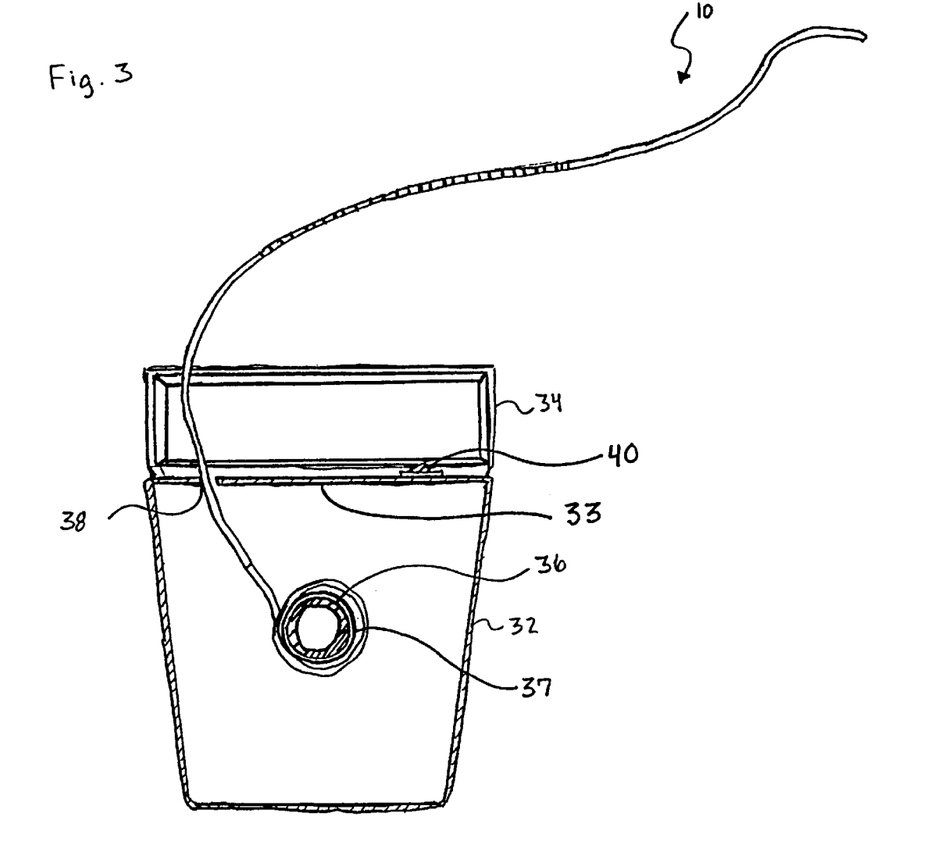
FIG. 3 is a section view of the dental floss package shown in FIG. 1.

As shown in FIG. 2, the dental floss 10 is contained within a dispenser 30. The dispenser 30 includes a housing 32 on which a cap 34 is provided. Turning briefly to FIG. 3, the housing 32 includes an axle 36 that rotatably supports a reel 37 around which the dental floss 10 is wound. A top wall 33 of the housing 32 includes an aperture 38 through which the dental floss 10 passes upon being dispensed.

Turning back to FIG. 2, the top wall 33 of the housing 32 is provided with a well known clipping device 40 for cutting the dental floss 10 at the desired length. The dispenser 30 also includes tamper proof seals 42 which ensure that the floss has not been tampered with before and after purchase by the consumer. The seals 42 also prevent a child from prying the housing 32 open in an effort to cheat the verification system, which is discussed in detail below.

The structural details of many types of dental floss dispensers are well known in this art and therefore a detailed discussion of the same is omitted. It is to be appreciated that the present invention can be implemented with other conventional dispensers.

III. The Verification System

The present invention provides a regimen verification system via a specially marked floss segment 100, a location indicator 50, and date indicator 60.

As shown in FIG. 2, the dental floss 10 includes a specially marked floss segment 100 (or "rainbow segment"). The specially marked floss segment 100 is provided along the length of the dental floss 10 that is unknown to the floss user. The specially marked floss segment 100 can be used to floss, just like any other colored floss segment. In this embodiment, the special marking includes a series of colored rings arranged sequentially along the length of the specially marked floss segment 100. However, the special markings may include a variety of other markings so long as the specially marked floss segment 100 is distinguishable from the other colored floss segments.

A location indicator 50 is packaged with the dental floss 10. Preferably, but not necessarily, the location indicator 50 may be an envelope or card that is temporarily fixed to the dispenser 30 via a tape 52. The location indicator 50 provides information to the parent. This information includes number information that represents the specific location of the specially marked floss segment 100 into the length of the dental floss 10. For example, the location indicator 50 may indicate that the specially marked segment is the 24th floss segment into the length of the dental floss 10. If this were the case, then the 24 would be the number information. It is to be appreciated that from one package to the next, the number information on the location indicator 50 could be varied, which would enhance the effectiveness of the verification system.

Figure 4:
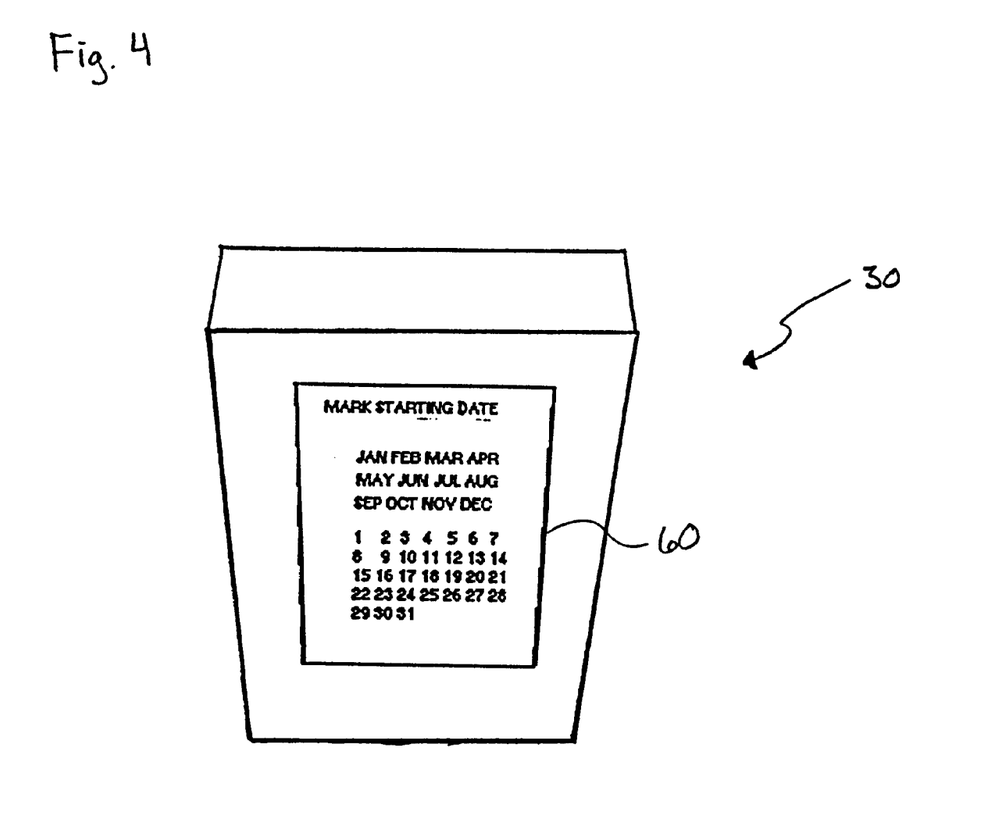
FIG. 4 is a rear view of the dental floss package shown in FIG. 1.

Turning to FIG. 4, a date indicator 60 is provided on the back side of the dispenser 30. The date indicator 60 provides a place to record the date on which the use of that particular dental floss 10 was initiated. For example, if the child begins using the floss package on June 7, then the parent would mark the date indicator 60 by circling "JUN" and "7". In this embodiment, the date indicator 60 is conveniently provided as a sticker adhered to the dispenser 30. However, the date indicator 60 may also be packaged with the dispenser 30, and separatable therefrom.

IV. An Illustrative Scenario

The use verification system will be better appreciated by considering the following illustrative scenario, which is non-limiting. The parent, having purchased the dental floss package, removes the location indicator 50 from the dispenser 30. The location indicator 50 is concealed from the child. Assume the location indicator 50 indicates that the "rainbow segment" is the 24th floss segment into the length of the dental floss 10. That is, the number information is 24.

The parent then instructs the child to remove a single floss segment every day and floss with it: this assumes that the desired flossing regimen involves flossing on a daily basis. The parent also instructs the child to notify the parent when the "rainbow segment" is encountered. The parent records the date that the child begins using the floss package on the date indicator 60. For extra encouragement, the parent may instruct the child that a reward will follow if the flossing regimen is adhered to.

The child proceeds to floss, presumably on a daily basis. Eventually, the child encounters the "rainbow segment" of floss. On that day, the child notifies the parent. The parent then uses a calendar (or alternatively a simple calculating device) to determine the length of the flossing regimen: that is, how long the child has been using the dental floss package. More specifically, the parent determines the number of days from (and including) the start date recorded on the date indicator 60 to (and including) the day on which the notification occurs. This number of days is then compared to the number information (i.e., 24) provided on the location indicator 50. One of the following three outcomes is possible.

Outcome 1: The child notifies the parent on the 24th day of use, which would yield a regimen length calculation result that is equal to the number information shown on the location indicator 50. This outcome would tend to show that the child adhered to the flossing regimen admirably.

Outcome 2: The child notifies the parent after the 24th day of use, which would yield a regimen length calculation result that is greater than the number information shown on the location indicator 50. This outcome would tend to show that the child did not floss on some days. The number of days without flossing is the difference between (1) the number of days the child has been using the dental floss package and (2) the number information on the location indicator 50. For example, if the child notifies the parent on the 34th day of use, then the number of days without flossing would be determined as 10 (i.e., 34−24).

Outcome 3: The child notifies the parent before the 24th day of use, which would yield a regimen length calculation result that is less than the number information shown on the location indicator 50. This outcome would tend to show that the child either incorrectly used more than one colored floss segment per day, or otherwise may have attempted to "cheat the system."

The above scenario is based on the child being instructed to floss on a daily basis. It is to be appreciated, however, that the invention is not so limited and that the verification system can be successfully implemented with other floss frequencies. For example, if the child were instructed to floss every other day, then the parent would expect the child's notification of the specially marked floss segment 100 to occur on the 48th day (i.e., 2×24), at least based on the number information of 24 provided on the location indicator 50 in the above scenario.

V. The Calculation Tool

Figure 5A:
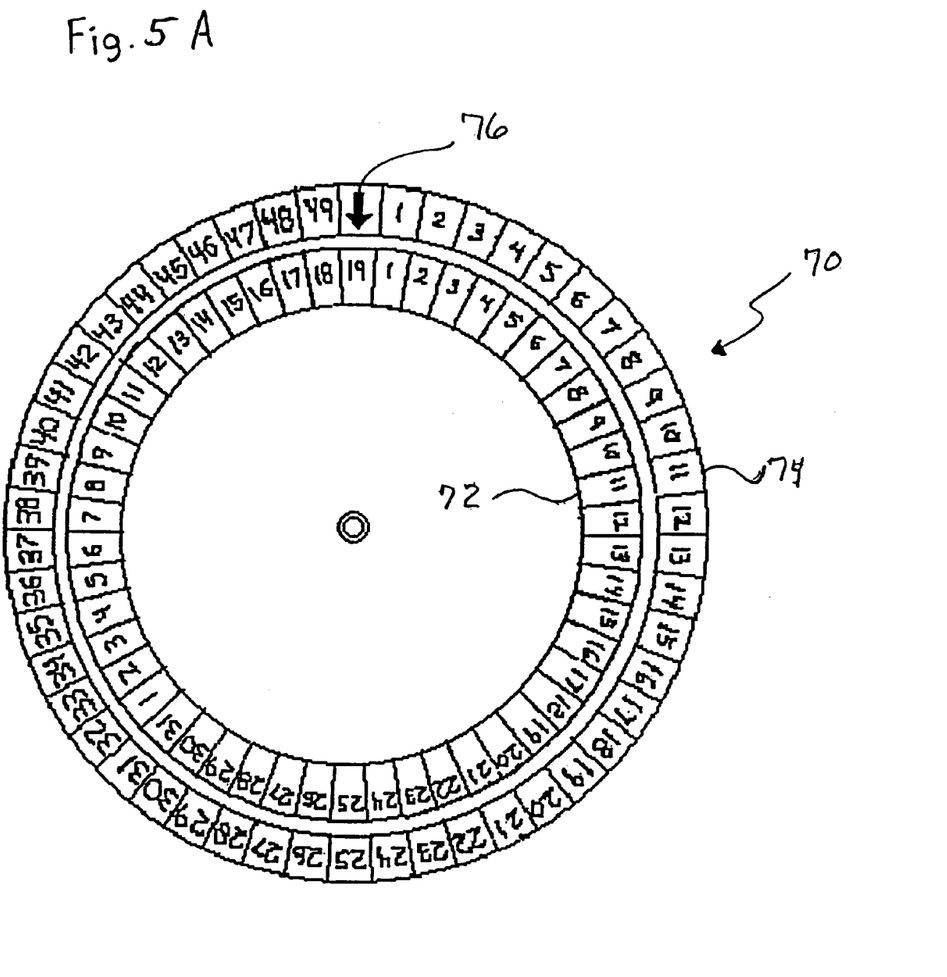
FIGS. 5A and 5B are plan views of a calculating tool according to an illustrative, non-limiting embodiment of the present invention.

As noted the above, the parent may use a calendar to determine the length of the flossing regimen. That is, how long (in days) that the dental floss package has been in use by the child. In the alternative (or in addition to the calendar), the parent may use a calculation tool for the same purpose. One embodiment of a calculation tool 70 is illustrated in FIG. 5A. The calculation tool 70 includes two concentric rings 72, 74 that are rotatable with respect to each other. Both of the rings 72, 74 are numbered. The numbers on the inner ring 72 represent the days of the month. The numbers on the outer ring 74 provide a counting feature. The outer ring 74 also includes an arrow 76.

The calculation tool 70 is used as follows. The arrow 76 on the outer ring 74 is aligned with the day on the inner ring 72 on which the regimen is started. The parent then determines the approximate length of the regimen from the number of the outer ring 74 that is aligned with the number on the inner ring 72 that correspond to the day of the month on which the child's notification occurred. This determination may then be compared to the number information recorded on the location indicator 50.

Figure 5B:
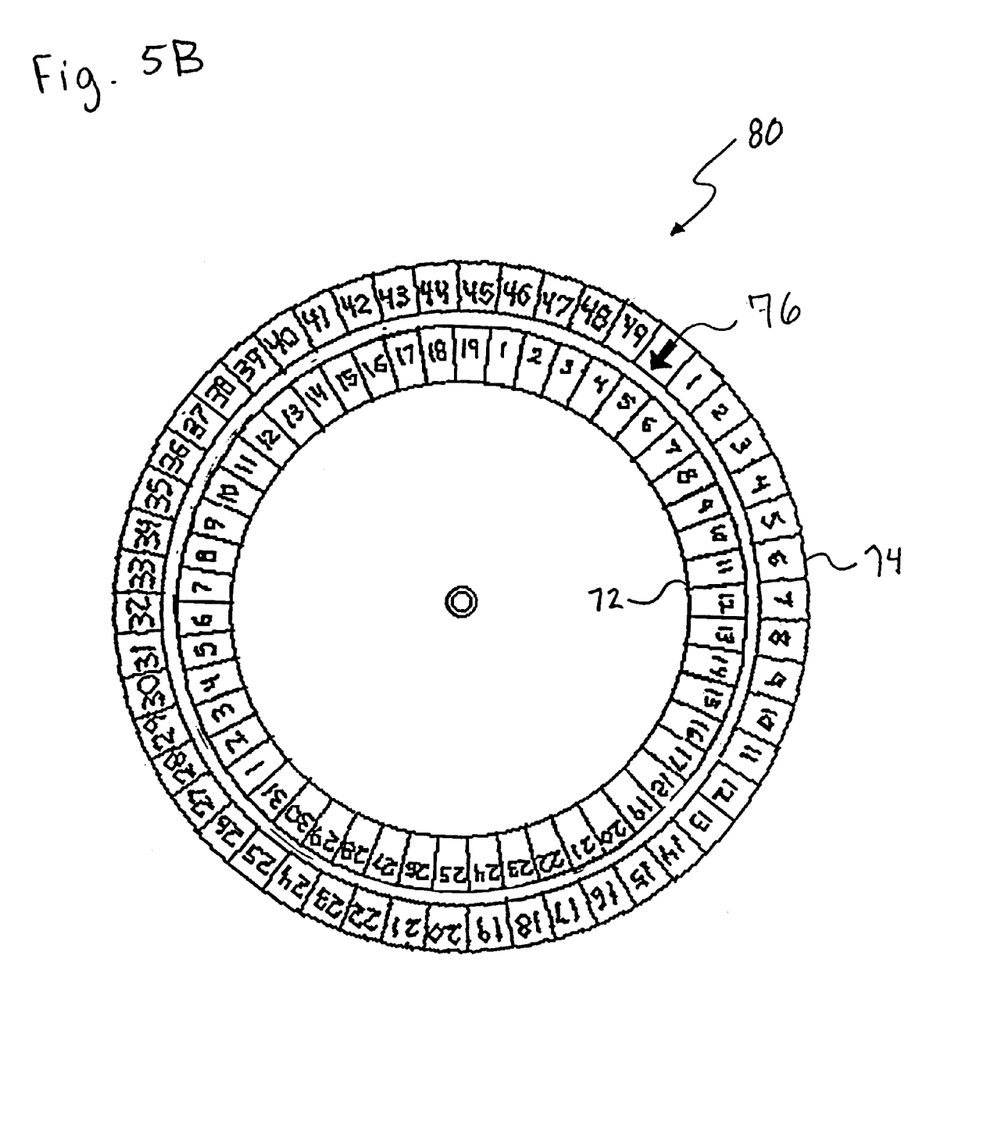

Example: Assume the number information is 24, and that the regimen is started on the fifth day of the month. As shown in FIG. 5B, the outer ring 74 would be rotated clockwise (relative to the inner ring 72) so that the arrow 76 aligns with the number "5" on the inner ring 72. Further assume that the child notifies the parent of the specially marked floss segment 100 on the 29th day of the same month. The "29" on the inner ring 72 is aligned with the "24" on the outer ring 74. Thus, the length of the flossing regimen is determined to be 24 days long, which is equal to the number information provided on the location indicator 50. This would tend to show that the child adhered to the flossing regimen admirably.

It is to be appreciated that the calculation tool 70 provides an estimate of the flossing regimen's length. Most of the time the estimate will be accurate; but sometimes the estimate will contain an error ranging from 0 to +3 days. The error occurs because the inner ring 72 of the calculation tool 70 is based upon a 31 day month. The estimated regimen length should be close enough for use by the verification authority (i.e., the parent). However, if an exact value is desired, then the correction chart 80 shown in FIG. 6 can be used in combination with the calculation tool 70. The correction chart 80 in FIG. 6 sets forth the number of days to be subtracted from the estimated regimen length obtained via the calculation tool 70. The data on the correction chart 80 will correct an estimated length of a regimen that extends through the end of a month that has less than 31 days.

Figure 6:
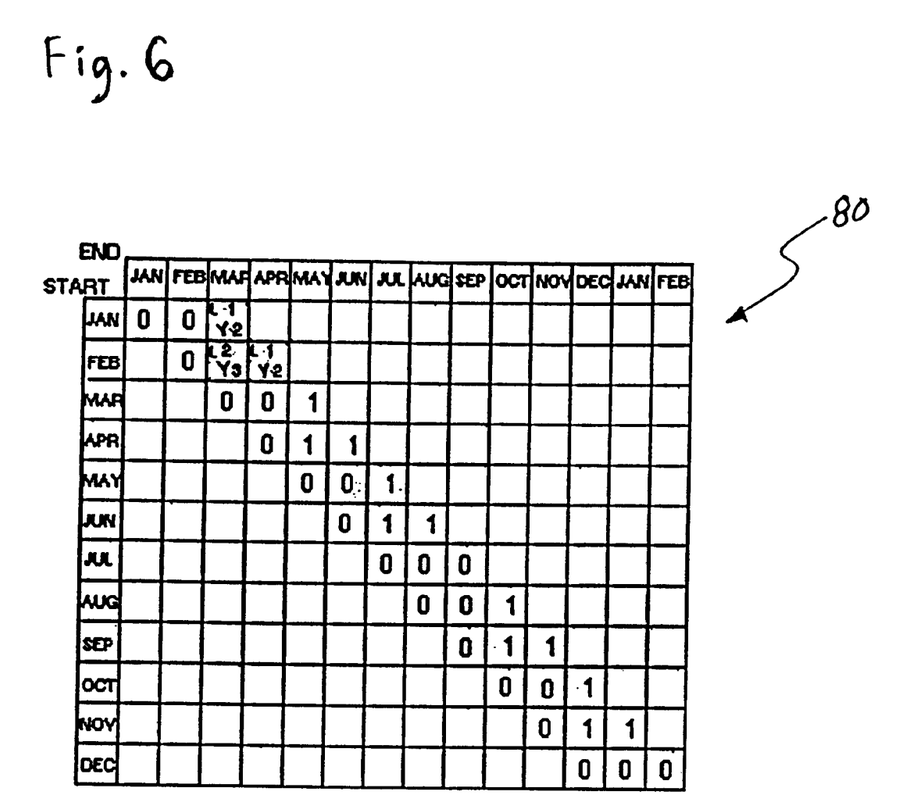
FIG. 6 is a plan view of a correction chart according to an illustrative, non-limiting embodiment of the present invention.

Continuing with the example discussed above (i.e., the number information is 24, and the regimen is started on the fifth day of the month), further assume that the starting date occurs on the fifth day of February and that the child's notification occurs on the first day of March. As shown in FIG. 5B, the "1" on the inner ring 72 (which corresponds to the first day of March) is aligned with the "27" on the outer ring 74. Thus, the length of the flossing regimen is estimated to be 27 days long, which is greater than the number information provided on the location indicator 50. However, February only has 28 days (not 31 days), and therefore the estimated regimen length includes an error. This error may be corrected by referring to the correction chart 80: specifically, the data set forth at the intersection of the row labeled "FEB" (i.e., the start month) and the column labeled "MAR" (i.e., the end month). This data is set forth as "L 2, Y 3". The "L" refers to a leap year and the "Y" refers to a non-leap year. Assuming the year in this example is not a leap year, then the days to be subtracted from the estimated regimen length would be 3, and the corrected length of the flossing regimen would be 24 days long (i.e., 27–3), which is equal to the number information provided on the location indicator 50. This would tend to show that the child adhered to the flossing regimen admirably.

It will be appreciated that a common calendar can be used to determine the exact length of the flossing regimen. But it may be more convenient to use a calculation tool 70 instead. The calculation tool 70 will accurately approximate the length of the flossing regimen over 50% of the time. But for cases where the approximation does include an error, a quick reference to the correction chart 80 will indicate the number of days to be subtracted from the approximation, thereby correcting the approximation. The calculation tool 70 and the correction chart 80 may be provide along with the dental floss package.

The calculation tool 70 and the correction chart 80 can be fabricated from cardboard, for example. The use of cardboard materials makes fabrication easy and cheap.

A dental floss package according to the present invention provides many advantages over conventional packaging techniques. Namely, the contrasting colored floss segments of recommended length for each use reinforce the habit of taking off the appropriate length of floss. The invention includes a built in verification system based upon the number of colored floss segments used and calendar date. The verification system can be used by an authority (e.g., a parent) to assess how often their subordinate (e.g., a child) is flossing. The verification system constitutes a basis for establishing good flossing habits based upon a system of positive reinforcement.

What is claimed is:

1. A dental floss package comprising:

a dispenser;

a dental floss provided in the dispenser, the dental floss having a plurality of floss segments, each floss segment defining a usable length of the dental floss for a single flossing, one of the floss segments being specially marked; and indicator means for indicating a location of the specially marked floss segment along the length of the dental floss.

2. The dental floss package according to claim 1, wherein the location of the specially marked floss segment is indicated as a number of floss segments into the dental floss from a dispensing end of the dental floss.

3. The dental floss package according to claim 1, wherein the indicator means is removably attached to the dispenser.

4. The dental floss package according to claim 3, wherein the indicator means is one of an envelope and a card.

5. The dental floss package according to claim 1, further comprising a date indicator on which a use start date is recordable.

6. The dental floss package according to claim 5, wherein the date indicator is a sticker adhered to the dispenser.

7. The dental floss package according to claim 6, wherein the date indicator includes month information and day information.

8. The dental floss package according to claim 1, further comprising a calculation tool adapted to approximate a length of a flossing regimen that extends from a use start date to a date on which the specially marked floss segment is encountered.

9. The dental floss package according to claim 8, further comprising a correction chart that contains data for correcting the approximation from the calculation tool.

10. A dental floss package comprising:

a dispenser;

a dental floss provided in the dispenser, the dental floss having a plurality of floss segments, each floss segment defining a usable length of the dental floss for a single flossing, one of the floss segments being specially marked;

a location indicator that indicates a location of the specially marked floss segment along the length of the dental floss; and a calculation tool adapted to approximate a length of a flossing regimen that extends from a use start date to a date on which the specially marked floss segment is encountered, wherein the calculation tool comprises a first ring concentrically provided within a second ring, the first and the second rings being rotatable with respect to each other.

11. A method to verify adherence to a flossing regimen, the method comprising the steps of:

provide a dental floss having a plurality of floss segments, each floss segment defining a usable length of the dental floss for a single flossing, one of the floss segments being specially marked;

providing a location indicator that indicates location information of the specially marked floss segment along the length of the dental floss;

initiating a flossing regimen on a start date;

noticing an end date when the specially marked floss segment is encountered;

determining a length of the flossing regimen, which extends from the start date to the end date.

12. The method according to claim 11, further comprising the step of:

comparing the length of the flossing regimen to the location information.

13. The method according to claim 11, wherein the length of the flossing regimen is determined in terms of days.

14. The method according to claim 11, wherein the flossing regimen involves periodic flossing with a different floss segment.

15. The method according to claim 14, wherein the periodic flossing occurs on a daily basis.

* * * * *